(12) United States Patent
Bodner

(10) Patent No.: US 11,793,971 B2
(45) Date of Patent: Oct. 24, 2023

(54) CURVED CATHETER FOR INCREASED INTRATHECAL DRUG DISPERSION

(71) Applicant: Medtronic, Inc., Minneapolis, MN (US)

(72) Inventor: Jeffrey Bodner, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1139 days.

(21) Appl. No.: 16/508,442

(22) Filed: Jul. 11, 2019

(65) Prior Publication Data

US 2020/0016368 A1    Jan. 16, 2020

Related U.S. Application Data

(60) Provisional application No. 62/697,537, filed on Jul. 13, 2018.

(51) Int. Cl.
| | | |
|---|---|---|
| *A61M 25/00* | (2006.01) | |
| *A61M 5/142* | (2006.01) | |
| *A61K 9/00* | (2006.01) | |
| *A61M 5/145* | (2006.01) | |

(52) U.S. Cl.
CPC .... *A61M 25/0068* (2013.01); *A61M 5/14276* (2013.01); *A61M 25/0043* (2013.01); *A61K 9/0085* (2013.01); *A61M 5/145* (2013.01); *A61M 2025/0057* (2013.01)

(58) Field of Classification Search
CPC ........ A61M 2025/0073; A61M 25/007; A61M 27/006; A61M 2025/0057; A61M 25/0043; A61M 25/0068; A61M 5/14276; A61M 5/145; A61K 9/0085
See application file for complete search history.

(56) References Cited

U.S. PATENT DOCUMENTS

| | | | |
|---|---|---|---|
| 4,502,488 | A | 3/1985 | Degironimo et al. |
| 4,730,623 | A | 3/1988 | Lee |
| 4,834,709 | A | 5/1989 | Banning et al. |

(Continued)

FOREIGN PATENT DOCUMENTS

| | | |
|---|---|---|
| EP | 0226220 A2 | 6/1987 |
| EP | 1 345 640 B1 | 9/2003 |

(Continued)

OTHER PUBLICATIONS

International Search Report and Written Opinion for PCT/US2020/058462, dated Apr. 8, 2021, 13 pages.

(Continued)

*Primary Examiner* — Brandy S Lee
(74) *Attorney, Agent, or Firm* — Patterson Thuente, P.A.

(57) ABSTRACT

An intrathecal drug delivery system configured to improve dispersion of medicament with cerebral spinal fluid in a subarachnoid space of a patient. The intrathecal drug delivery system including an implantable medical pump and a catheter having a wall defining a lumen extending between a proximal end in fluid communication with the implantable pump and structure defining a medicament exit positionable within the subarachnoid space of the patient, the wall further defining at least one feature configured to generate vortices within the cerebrospinal fluid for the purpose of improving intrathecal drug dispersion.

13 Claims, 9 Drawing Sheets

(56) References Cited

U.S. PATENT DOCUMENTS

| | | |
|---|---|---|
| 5,807,324 A | 9/1998 | Griffin, III |
| 5,897,528 A | 4/1999 | Schultz |
| 5,931,805 A | 8/1999 | Brisken |
| 6,013,051 A | 1/2000 | Nelson |
| 6,579,280 B1 | 6/2003 | Kovach et al. |
| 6,807,965 B1 | 10/2004 | Hickle |
| 7,072,802 B2 | 7/2006 | Hartlaub |
| 7,192,414 B2 | 3/2007 | Stultz |
| 7,438,701 B2 | 10/2008 | Theeuwes et al. |
| 7,593,770 B2 | 9/2009 | Lerner |
| 7,651,518 B2 | 1/2010 | Dobak, III et al. |
| 7,806,886 B2 | 10/2010 | Kanderian et al. |
| 8,486,023 B2 | 7/2013 | Pyles |
| 9,122,785 B2 | 9/2015 | Alme et al. |
| 9,655,528 B2 | 5/2017 | Zhu |
| 9,682,193 B2 | 6/2017 | Anand et al. |
| 2001/0044588 A1 | 11/2001 | Mault |
| 2005/0277803 A1* | 12/2005 | Pecor ............... A61M 5/14276 600/16 |
| 2006/0064009 A1 | 3/2006 | Webler et al. |
| 2006/0178617 A1 | 8/2006 | Adams et al. |
| 2007/0073250 A1 | 3/2007 | Schneiter |
| 2007/0137296 A1 | 6/2007 | Krivitski et al. |
| 2008/0146990 A1 | 6/2008 | Jenson et al. |
| 2010/0125246 A1 | 5/2010 | Kalpin |
| 2011/0238039 A1 | 9/2011 | Leonard et al. |
| 2011/0245766 A1 | 10/2011 | Leonard et al. |
| 2012/0245562 A1 | 9/2012 | Bihlmaier |
| 2012/0302938 A1 | 11/2012 | Browd et al. |
| 2013/0267928 A1 | 10/2013 | Imran |
| 2013/0296823 A1 | 11/2013 | Melker et al. |
| 2013/0324892 A1 | 12/2013 | Zhu et al. |
| 2014/0228765 A1 | 8/2014 | Burke et al. |
| 2015/0297874 A1 | 10/2015 | East et al. |
| 2016/0331897 A1 | 11/2016 | Anand et al. |
| 2017/0203084 A1 | 7/2017 | Lad et al. |
| 2018/0185058 A1* | 7/2018 | Anand ............... A61M 5/3286 |
| 2019/0160254 A1 | 5/2019 | Anand et al. |
| 2019/0388663 A1 | 12/2019 | Bodner et al. |
| 2020/0016368 A1 | 1/2020 | Bodner et al. |
| 2020/0125246 A1 | 4/2020 | Stephens et al. |

FOREIGN PATENT DOCUMENTS

| | | |
|---|---|---|
| WO | WO 2004100769 A2 | 11/2004 |
| WO | WO 2006002275 A2 | 1/2006 |
| WO | WO 2011140118 A1 | 11/2011 |
| WO | WO 2017122199 A1 | 7/2017 |
| WO | WO 2018005169 A1 | 1/2018 |
| WO | WO2018119179 A1 | 6/2018 |

OTHER PUBLICATIONS

U.S. Appl. No. 16/508,442, filed Jul. 11, 2019, Inventor(s): Bodner et al.

U.S. Appl. No. 16/572,763, filed Sep. 17, 2019, Inventor(s): Bodner.

Office Action for EP Application No. 19179065.8, dated Sep. 10, 2020, 6 pages.

K. Tangen, I. Nestorov, A. Verma, J. Sullivan, R.W. Holt and A.A. Linninger, "In Vivo Intrathecal Tracer Dispersion in Cynomolgus Monkey Validates Wide Biodistribution Along Neuraxis," in IEEE Transactions on Biomedical Engineering, vol. 6, pp. 1122-1132, Apr. 2020 (Year: 2019).

Extended European Search Report for European Application No. 19185551.9, dated Dec. 18, 2019.

International Search Report and Written Opinion for PCT/US2020/043252, dated Oct. 5, 2020, 12 pages.

International Search Report and Written Opinion for PCTUS2020043249, dated Nov. 16, 2020, 10 pages.

Extended European Search Report for European Application No. 19179065.8, dated Aug. 9, 2019.

Sakka et al., "Anatomy and physiology of cerebrospinal fluid," European Annals of Otorhinolaryngology, Head and Neck diseases (2011) 128, 309-316. Available online Nov. 18, 2011.

* cited by examiner

VON KARMAN VORTEX TRAIL

CURVED CATHETER FOR INCREASED INTRATHECAL DRUG DISPERSION

RELATED APPLICATION INFORMATION

This application claims the benefit of U.S. Provisional Application No. 62/697,537, filed Jul. 13, 2018 the contents of which are fully incorporated herein by reference.

TECHNICAL FIELD

The present disclosure relates generally to implantable medical devices, and more particularly to a system and method utilizing a curved catheter for increased intrathecal drug dispersion.

BACKGROUND

A variety of medical devices are used for chronic, i.e., long-term, delivery of therapy to patients suffering from a variety of conditions, such as chronic pain, tremor, Parkinson's disease, cancer, epilepsy, urinary or fecal incontinence, sexual dysfunction, obesity, spasticity, or gastroparesis. For example, pumps or other fluid delivery devices can be used for chronic delivery of therapeutic medicaments, such as drugs or other agents. Typically, such devices provide therapy continuously or periodically according to programmed parameters. The programmed parameters can specify the therapeutic regimen (e.g., the rate, quantity, and timing of medicament delivery to a patient), as well as other functions of the medical device.

Implantable medical infusion pumps have important advantages over other forms of medicament administration. For example, oral administration is often not workable because the systematic dose of the substance needed to achieve the therapeutic dose at the target site may be too large for the patient to tolerate without adverse side effects. Also, some substances simply cannot be absorbed in the gut adequately for a therapeutic dose to reach the target site. Moreover, substances that are not lipid-soluble may not cross the blood-brain barrier adequately if needed in the brain. In addition, infusion of substances from outside the body requires a transcutaneous catheter, which results in other risks such as infection or catheter dislodgment. Further, implantable medical pumps avoid the problem of patient-noncompliance, namely the patient failing to take the prescribed drug or therapy as instructed.

Implantable medical infusion pumps are typically implanted at a location within the body of a patient (typically a subcutaneous region in the lower abdomen), and are configured to deliver a fluid medicament through a catheter. The catheter is generally configured as a flexible tube with a lumen running the length of the catheter to a selected delivery site in the body, such as the spinal canal or subarachnoid space. Such implantable medical pumps typically include an expandable fluid reservoir, which is accessible for refill etc. through an access port. Medicament flows from the reservoir via the lumen in the catheter according to programmed parameters.

Drug molecules exiting the catheter lumen flow into the subarachnoid space, and begin mixing with the cerebrospinal fluid. Frequently, the drug exits the catheter slowly (e.g., a flow rate of 1 mL per hour or less), where it tends to stagnate in the slow-moving cerebrospinal fluid immediately surrounding the catheter. This slow-moving fluid is known to those schooled in the science of fluid mechanics as a "boundary layer," which is a consequence of friction between a viscous fluid and a surface (i.e., the catheter). A slow or delayed mixing of the drug with the cerebrospinal fluid can decrease the efficacy of the drug and resultant therapeutic effect. Although various attempts have been made to improve drug dispersion within the cerebrospinal fluid, it is desirous to further improve the efficiency of intrathecal drug delivery. Applicants of the present disclosure have developed a system and method to address this concern.

SUMMARY OF THE DISCLOSURE

Embodiments of the present disclosure provide a system and method of utilizing the contours of a catheter positioned within the subarachnoid space of a patient to generate vortices within the natural flow of cerebrospinal fluid for the purpose of improving the dispersion of the infused medicament. For example, in one embodiment, the catheter can have a curve configured to orient a distal portion of the catheter substantially orthogonal to the natural flow of the cerebrospinal fluid, which can in turn promote mixing within the cerebrospinal fluid in the form of a von Kármán vortex street. Improved mixing in the vicinity of the catheter can improve the dispersion of the otherwise relatively slow-moving medicament dispensed from the catheter.

One embodiment of the present disclosure provides an intrathecal drug delivery system configured to improve dispersion of medicament with cerebrospinal fluid in a subarachnoid space of the patient. The intrathecal drug delivery system can include an implantable medical pump and a catheter. The catheter can have a wall defining a lumen extending between the proximal end in fluid communication with the implantable medical pump and a structure defining a medicament exit positionable within the subarachnoid space of the patient. The wall can further define at least one feature configured to generate vortices within the cerebrospinal fluid for the purpose of improving intrathecal drug dispersion.

In one embodiment, the at least one feature can be a curve defined by the catheter wall configured to orient a distal portion of the catheter at an angle with respect to a proximal portion of the catheter. In one embodiment, the curve can be configured to orient the distal portion substantially orthogonal to a natural flow of cerebrospinal fluid within the subarachnoid space. In one embodiment, the distal portion can induce a von Kármán vortex street within the cerebrospinal fluid. In one embodiment, the distal portion can induce turbulence within the cerebrospinal fluid. In one embodiment, the medicament exit can be positioned to expel medicament in axial alignment with a natural flow of the cerebrospinal fluid within the subarachnoid space. In one embodiment, the catheter can be manipulated between an insertion position and an infusion position. In one embodiment the catheter can be configured to assume a sinusoidal shape. In one embodiment, multiple portions of the catheter can be positioned at a substantially orthogonal angle relative to a natural flow of cerebrospinal fluid within the subarachnoid space. In one embodiment, the at least one feature is at least one of a V-shaped ridge, spiral ridge, shelf, or a combination thereof configured to generate vortices in the presence of a moving fluid.

Another embodiment of the present disclosure provides a method of intrathecal drug delivery configured to improve dispersion of medicament with cerebrospinal fluid in a subarachnoid space of the patient. The method can comprise dispensing medicament from an implantable medical infusion device into the subarachnoid space the patient; and utilizing at least one feature defined by catheter of the implantable medical infusion device to promote mixing within the cerebrospinal fluid for the purpose of improving intrathecal drug dispersion.

In one embodiment, the at least one feature is a curve defined by catheter wall configured to orient a distal portion of the catheter at an angle with respect to a proximal portion of the catheter. In one embodiment, the curve is configured to orient the distal portion substantially orthogonal to a natural flow of the cerebrospinal fluid within the subarachnoid space. In one embodiment, the distal portion can generate vortices within the cerebrospinal fluid. In one embodiment, the distal portion can induce turbulence within the cerebrospinal fluid.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1:
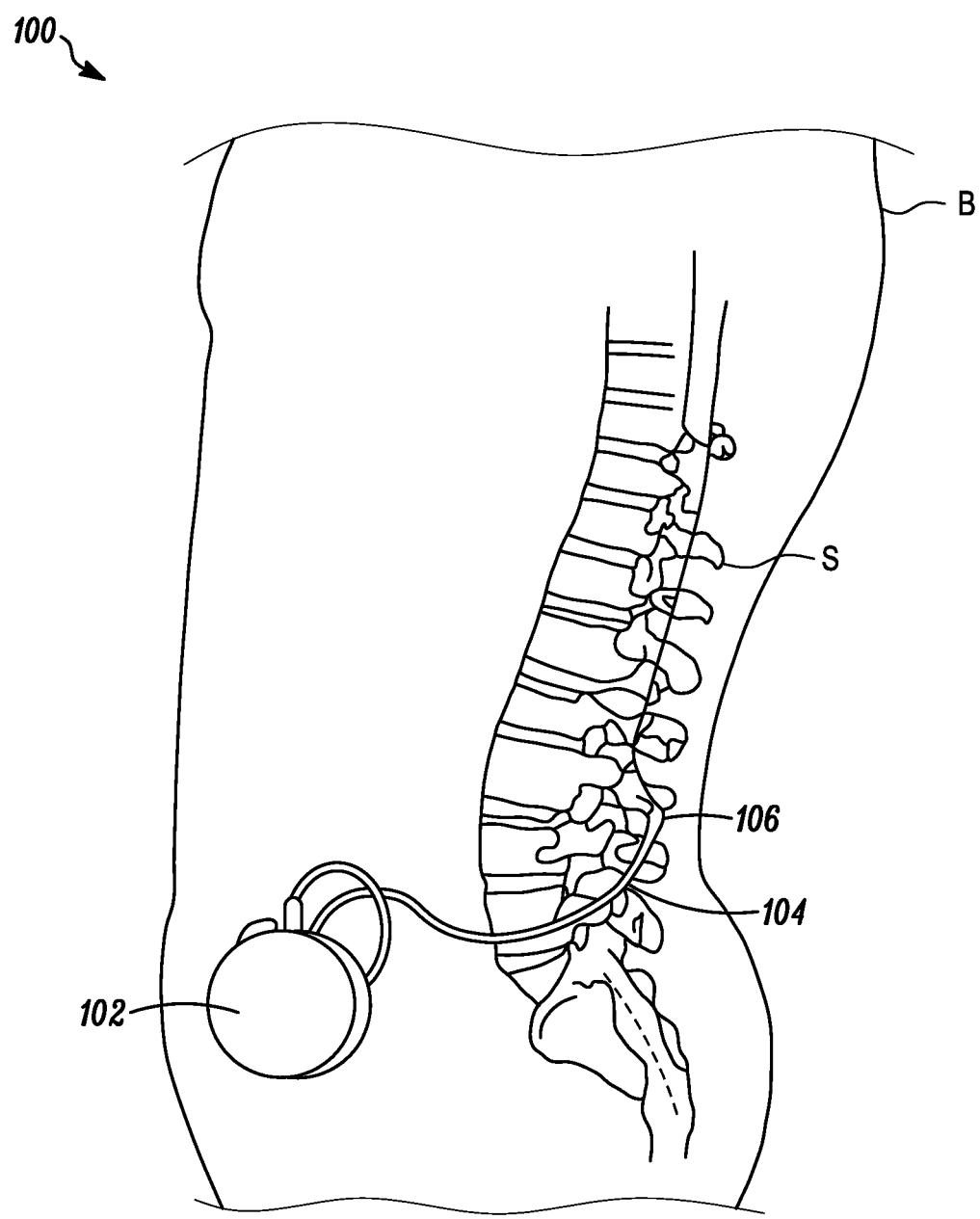
FIG. 1 depicts an intrathecal drug delivery system in accordance with an embodiment of the disclosure implanted within a body of a patient.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, an intrathecal drug delivery system 100 is depicted in accordance with an embodiment of the disclosure. The intrathecal drug delivery system 100 can include an implantable medical pump 102 and a catheter 104. As depicted, the implantable medical pump 102 can be implanted within the body B of a patient. The implantable medical pump 102 can be in fluid communication with the catheter 104 having a distal tip 106 positioned within the subarachnoid space of the patient's spinal column S, thereby enabling intrathecal delivery of medicament through a lumen of the catheter 104.

Figure 2:
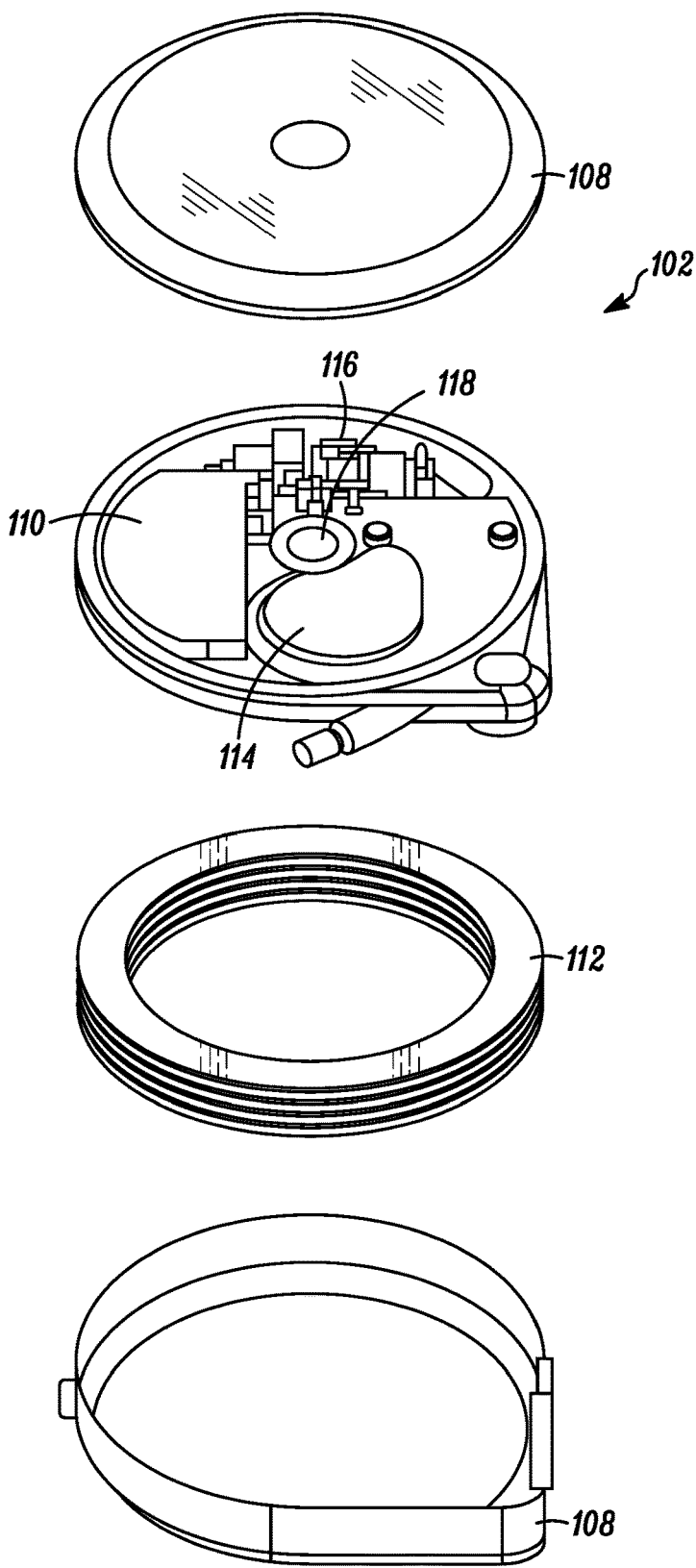
FIG. 2 is an exploded perspective view depicting an implantable medical pump in accordance with an embodiment of the disclosure.
Figure 3:
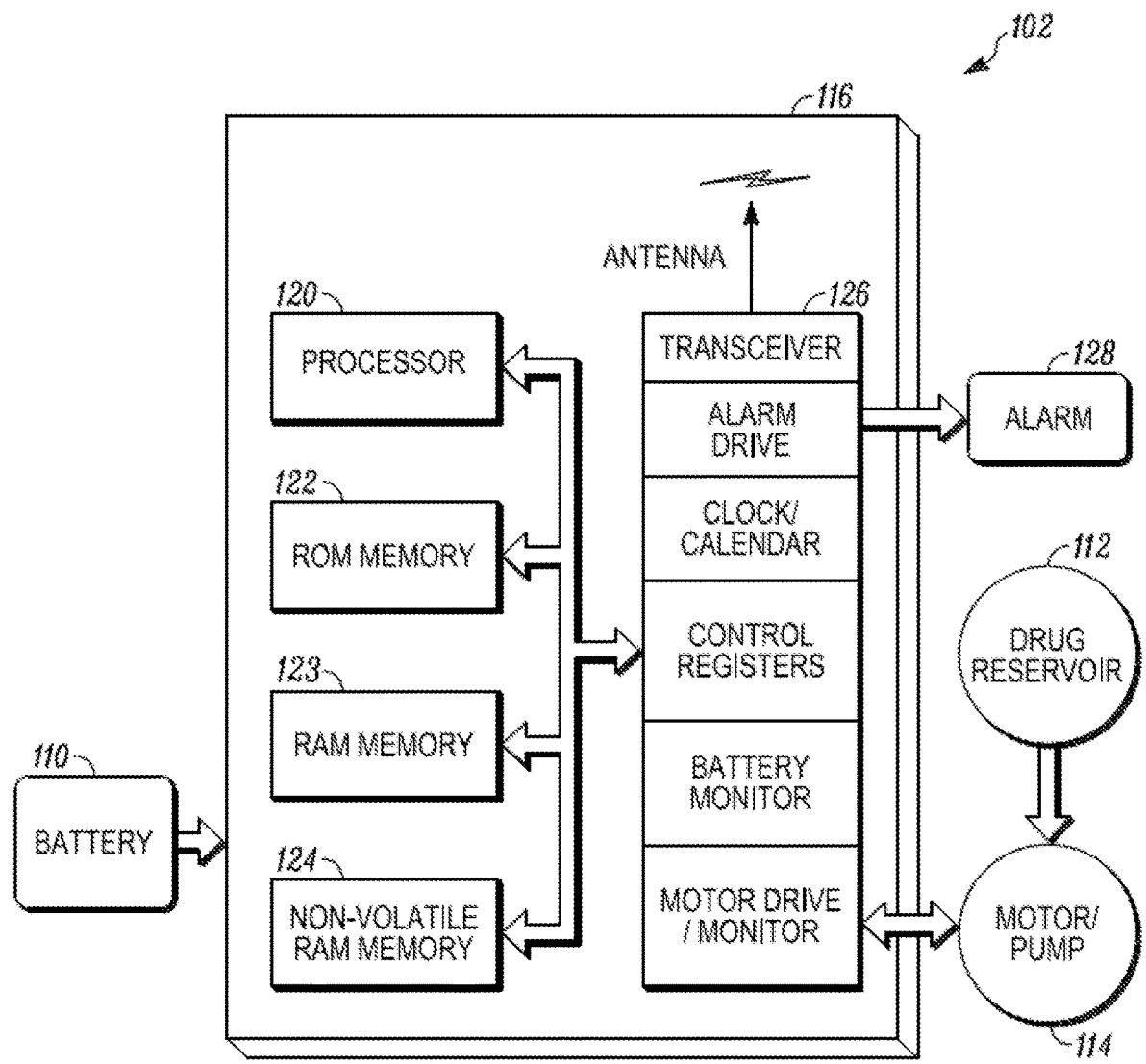
FIG. 3 is a block diagram depicting an implantable medical pump in accordance with an embodiment of the disclosure.

Referring to FIG. 2, an exploded perspective view of an implantable medical pump 102 is depicted in accordance with an embodiment of the disclosure, and referring to FIG. 3, a block diagram of an implantable medical pump 102 is depicted in accordance with an embodiment of the disclosure. The implantable medical pump 102 can generally include a housing 108, power source 110, medicament reservoir 112, medicament pump 114, and electronics 116. The housing 108 can be constructed of a material that is biocompatible and hermetically sealed, such as titanium, tantalum, stainless steel, plastic, ceramic, or the like. The power source 110 can be a battery, such as a lithium-ion battery. The power source 110 can be carried in the housing 108, and can be selected to operate the medicament pump 114 and electronics 116.

The medicament reservoir 112 can be carried by the housing 108 and can be configured to contain medicament. In one embodiment, medicament within the medicament reservoir 112 can be accessed via an access port 118. Accordingly, the access port 118 can be utilized to refill, empty, or exchange the fluid within the medicament reservoir 112.

The medicament pump 114 can be carried by the housing 108. The medicament pump 114 can be in fluid communication with the medicament reservoir 112 and can be in electrical communication with the electronics 116. The medicament pump 114 can be any pump sufficient for infusing medicament to the patient, such as a piston pump, a peristaltic pump, a pump powered by a stepper motor, a pump powered by an AC motor, a pump powered by a DC motor, an electrostatic diaphragm, a piezoelectric motor, a solenoid, a shape memory alloy, or the like.

The electronics 116 are carried in the housing 108, and can be in electrical communication with the power source 110 and medicament pump 114. In one embodiment, the electronics 116 can include a processor 120, memory 122/123/124, and transceiver circuitry 126. In one embodiment, the processor 120 can be an Application-Specific Integrated Circuit (ASIC) state machine, gate array, controller, or the like. The electronics 116 can be generally configured to control infusion of medicament according to programmed parameters or a specified treatment protocol. The programmed parameters or specified treatment protocol can be stored in the memory 122/123/124. The transceiver circuitry 126 can be configured to receive information from an external programmer (not depicted). In one embodiment, the electronics 116 can be further be configured to operate a number of other features, such a patient alarm 128.

The distal tip 106 of the catheter 104 can extend into the subarachnoid space of a patient's spine, thereby enabling delivery of medicament into the cerebrospinal fluid of the patient. The cerebrospinal fluid resides within the brain ventricles and the cranial and spinal subarachnoid spaces. Cerebrospinal fluid circulation is a dynamic phenomenon closely correlated with the patient's arterial pulse wave; although other factors, such as respiratory waves, the patient's posture, jugular venous pressure, and physical effort may also affect cerebrospinal fluid flow dynamics and pressure. The cerebrospinal fluid volume is estimated to be about 150 mL in adults, with approximately 125 mL located in the cranial and spinal subarachnoid spaces and the remaining 25 mL located in the brain ventricles. Through normal pulsatile flow, the cerebrospinal fluid is renewed about four times every 24 hours.

Figure 4A:
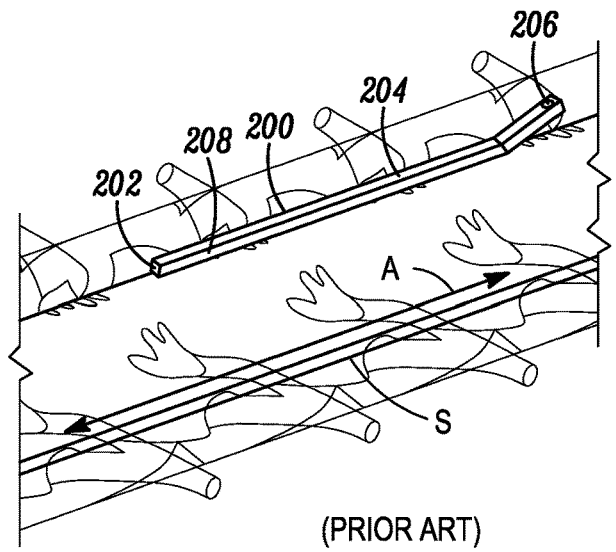
FIG. 4A is a perspective view depicting a catheter of the prior art inserted into a subarachnoid space of a patient.

Referring to FIG. 4A, a catheter 200 according to the prior art is depicted as being positioned within the subarachnoid space of a patient. The catheter 200, which can have a substantially circular cross section, can extend between a proximal end and a distal tip 202. The catheter 200 generally includes a wall 204 defining a lumen 206 extending between the proximal end and a medicament exit 208. The medicament exit 208 can be positioned on the distal tip 202 of the catheter. Alternatively, as depicted, the medicament exit 208 can be positioned proximally from the distal tip 202 along the wall 204 of the catheter 200.

The proximal end of the catheter 200 can be operably coupled to the implantable medical pump, such that the lumen 206 of the catheter 200 is in fluid communication with the medical pump 114 and reservoir 112. The catheter 200 enters the subarachnoid space at an insertion site, and extends substantially parallel to a longitudinal axis A of the patient's spinal column S, thereby enabling intrathecal delivery of medicament through the lumen of the catheter 104.

Figure 4B:
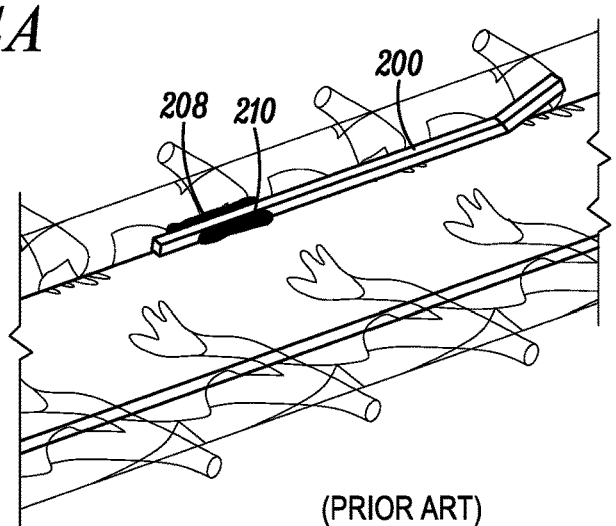
FIG. 4B depicts the dispersion of medicament within the cerebrospinal fluid of a patient after approximately 7.5 seconds of initiating infusion from the catheter of FIG. 4A at a rate of 1 mL per hour.
Figure 4C:
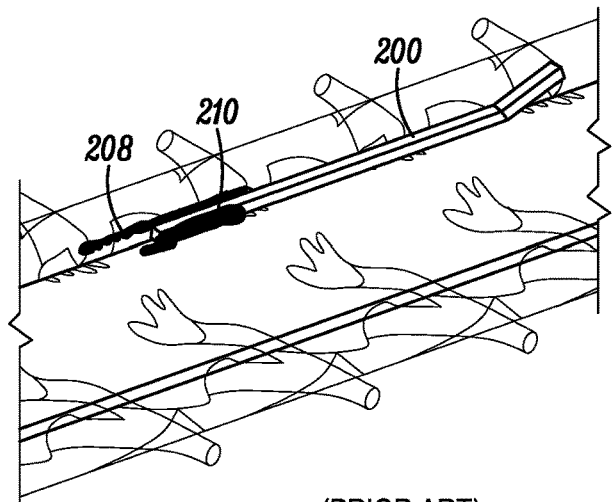
FIG. 4C depicts the dispersion of medicament within the cerebrospinal fluid of a patient after approximately 15 seconds of initiating infusion from the catheter of FIG. 4A at a rate of 1 mL per hour.

FIGS. 4B and 4C depict the catheter 200 as the medicament 210 exits the medicament exit 208 and flows into the subarachnoid space. Specifically, FIG. 4B depicts the dispersion of medicament 210 after approximately 7.5 seconds of initiating infusion, and FIG. 4C depicts the dispersion of medicament 210 after approximately 15 seconds of initiating infusion. As the medicament 210 exits the medicament exit 208 and flows into the subarachnoid space, the medicament 210 begins mixing with the cerebrospinal fluid. However, because the medicament 210 is expelled from the medicament exit 208 at a relatively slow rate (e.g., a flow rate of 1 mL per hour), the medicament 210 commonly stagnates in the slow-moving cerebrospinal fluid immediately surrounding the catheter 200. Although the pulsatile flow of the cerebrospinal fluid eventually causes the medicament 210 to drift away from the catheter 200 and into faster moving cerebrospinal fluid, proper mixing of the medicament 210 into the cerebrospinal fluid can take several minutes. A slow or delayed mixing of medicament with cerebrospinal fluid can decrease the efficacy of the medicament, as well as the resultant therapeutic effect.

Figure 5A:
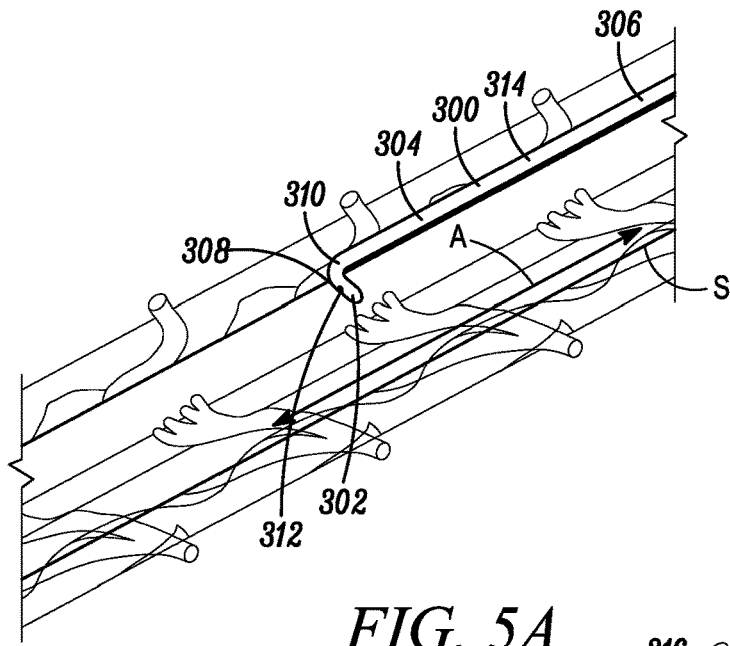
FIG. 5A is a perspective view depicting a catheter in accordance with an embodiment of the disclosure inserted into a subarachnoid space of a patient.

Referring to FIG. 5A, a catheter 300 configured for increased intrathecal drug dispersion is depicted in accordance with an embodiment of the disclosure. In one embodiment, the catheter 300 can include a generally circular cross-section, and can extend between a proximal end and a distal tip 302. Similar to conventional catheter designs, catheter 300 can generally include a wall 304 defining a lumen 306 extending between the proximal end and a medicament exit 308. However, unlike conventional catheter designs, catheter 300 can include one or more features 310 configured to generate vortices within the cerebrospinal fluid for the purpose of improving intrathecal drug dispersion.

For example, in one embodiment, the wall 304 of the catheter 300 can define a curved portion 310, such that a distal portion 312 of the catheter 300 is oriented substantially orthogonally to a proximal portion 314 of the catheter 300. Other angular orientations between the distal portion 312 and proximal portion 314 are also contemplated. Accordingly, a medicament exit 308, which can be positioned proximally from the distal tip 302 along the wall 304 of the catheter 300, can be positioned to expel medicament in-line with or parallel to the longitudinal axis A of the patient's spinal column S. In other words, the distal portion 312 (which can include the medicament exit 308) can be positioned substantially perpendicular to the flow of cerebrospinal fluid within the subarachnoid space, thereby generating vortices, inducing turbulence, or otherwise generally promoting mixing in the cerebrospinal fluid immediately surrounding the distal portion 312.

To promote ease in inserting the catheter 300 into the subarachnoid space of a patient, the catheter 300 can be manipulated between an insertion position and an infusion position. For example, in one embodiment, the catheter 300 can be constructed of a heat-setting polyurethane or similar material, which can be naturally biased to orient the distal portion 312 relative to the proximal portion 314 in the desired infusion position. During insertion of the catheter 300 into the subarachnoid space, a needle or stylet can be positioned within the lumen 306 to straighten the catheter 300, or otherwise inhibit the catheter 300 from assuming the infusion position.

The dispersion of medicament delivered via catheter 300 into the subarachnoid space can be simulated using computational fluid dynamics (CFD) modeling methods such as the well-known finite-volume, finite-element, or finite-difference techniques for finding approximate solutions to systems of partial differential equations. In the case of intrathecal delivery, the system of partial differential equations that model conservation of mass and momentum, also known as the Navier-Stokes equations, can simulate cerebrospinal fluid flow. To be more precise, the equations for laminar, oscillating flow of an incompressible fluid with properties similar to water at body temperature can be used to simulate medicament-delivery scenarios. Medicament dispersion can further be modeled using various techniques including the Eulerian passive scalar approach or the Lagrangian particle approach.

FIGS. 4A-C and FIGS. 5A-C represent predictions of the respective volumes of dispersed clouds of medicament in an idealized intrathecal space geometry with cerebrospinal fluid that oscillates according to a sine function with a 1 Hz frequency and 3 ml/s amplitude. With a nominal straight catheter 200 (such as that depicted in FIGS. 4A-C), at a time of 30 seconds after the start of a bolus infusion at 1 ml/hr, the infused medicament can occupy a volume of approximately 25 mm$^3$. By contrast, for a design where the tip of the catheter 300 is curved (such as that depicted in FIGS. 5A-C), with all other model parameters kept constant, the infused medicament can occupy a volume of approximately 500 mm$^3$. Thus, it can be seen that the one or more features 310 described above can have the effect of increasing the volume of dispersed medicament approximately 20 times that of prior art designs after 30 seconds of infusion. In some embodiments, bolus deliveries may be longer than a period longer than 30 seconds, and the presence of the medicament in the cerebrospinal fluid can last for several hours after infusion.

Figure 6:
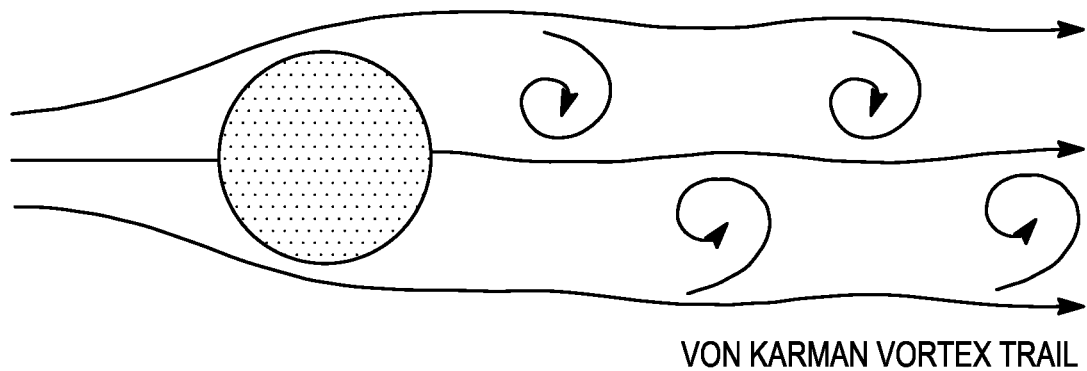
FIG. 6 depicts an example of a von Kármán vortex street.

Referring to FIG. 6, a cylindrical object positioned within a fluid flow can result in a repeating pattern of swirling vortices, caused by a process known as vortex shedding, which is responsible for the unsteady separation of flow of a fluid around blunt bodies. Such a fluid flow is commonly referred to in the field of fluid dynamics as a "von Kármán vortex street," and is responsible for such phenomena as the "singing" of suspended telephone power lines and the vibration of a car antenna at certain speeds.

Figure 7:
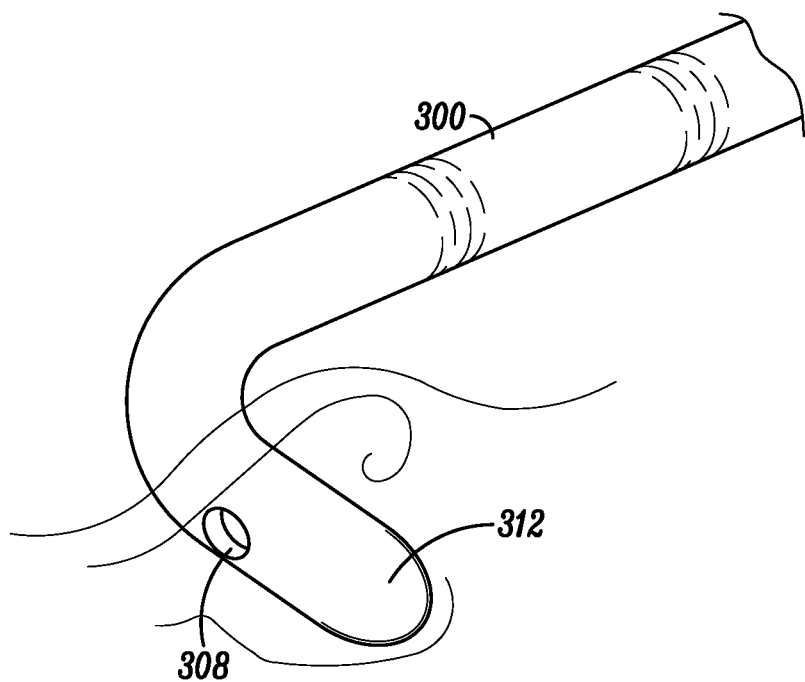
FIG. 7 is a perspective view depicting a catheter in accordance with an embodiment of the disclosure dispensing medicament within a von Kármán vortex street.

Referring to FIG. 7, in intrathecal drug delivery, positioning of the distal portion 312 perpendicular to the pulsatile flow of cerebrospinal fluid, can be used to generate a series of counter-rotating vortices to promote local mixing of the medicament with the cerebrospinal fluid along the flow direction, thereby carrying the medicament away from the relatively slow-moving fluid in the boundary layer of the catheter 300. Further, in some embodiments, the medicament exit 308 can be positioned within the subarachnoid space, such that the pulsatile flow of cerebrospinal fluid can act to push slow-moving or stagnant medicament out of the medicament exit 308 to further improve mixing.

Figure 5B:
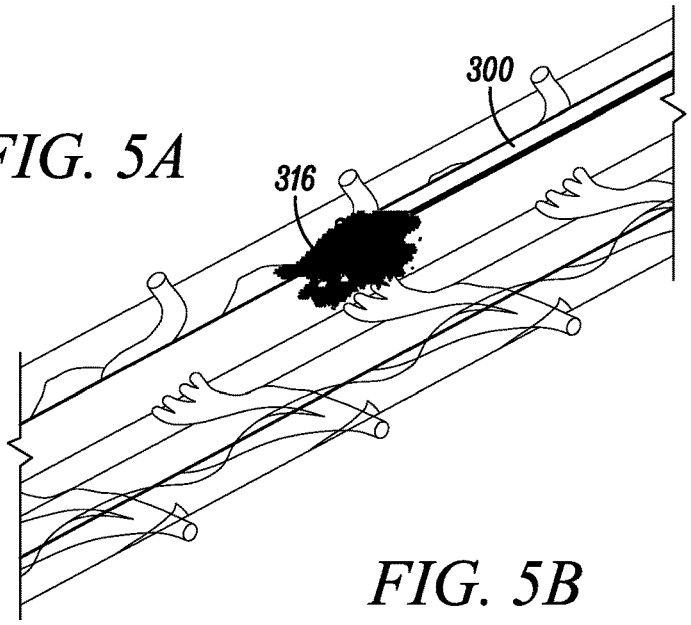
FIG. 5B depicts the dispersion of medicament within the cerebrospinal fluid of a patient after approximately 7.5 seconds of initiating infusion from the catheter of FIG. 5A at a rate of 1 mL per hour.
Figure 5C:
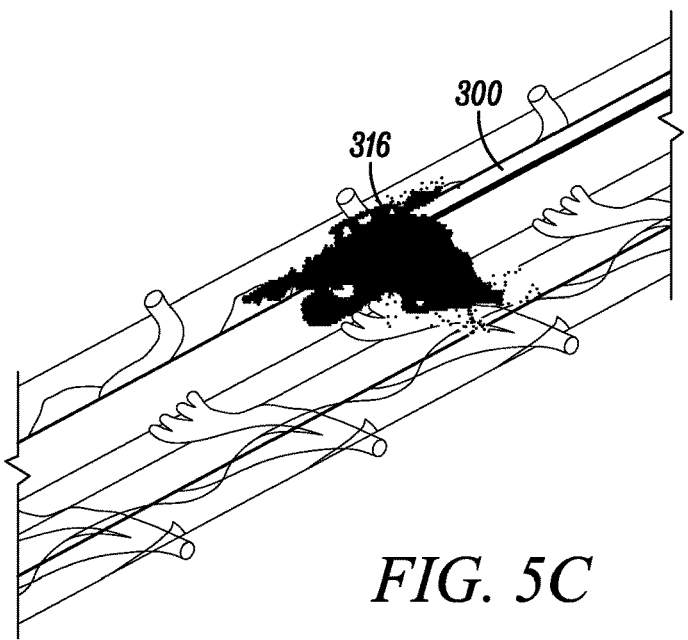
FIG. 5C depicts the dispersion of medicament within the cerebrospinal fluid of a patient after approximately 15 seconds of initiating infusion from the catheter of FIG. 5A at a rate of 1 mL per hour.

FIGS. 5B and 5C depict the catheter 300 as the medicament 316 exits the medicament exit 308 and flows into the subarachnoid space. Specifically, FIG. 5B depicts the dispersion of medicament 316 after approximately 7.5 seconds of initiating infusion, and FIG. 5C depicts the dispersion of medicament 316 after approximately 15 seconds of initiating infusion. As the medicament 316 exits the medicament exit 308 and flows into the subarachnoid space, the medicament 316 begins mixing with the cerebrospinal fluid. Despite the medicament 316 being expelled from the medicament exit 308 at the same relatively slow rate (e.g., a flow rate of 1 mL per hour) mixing of the medicament 316 with the cerebrospinal fluid is enhanced by the vortices generated by the catheter 300. In particular, the counter-rotating vortices of the von Kármán vortex street promote faster distribution of the medicament 316 throughout the cerebrospinal fluid by quickly transporting the medicament 316 away from the catheter 300 and into faster-moving cerebrospinal fluid. Accordingly, intrathecal infusion via catheter 300 enables dispersion of the medicament 316 to occur more rapidly than infusion via conventional methods (particularly in comparison to the infusion method depicted in FIGS. 4A-B), thereby increasing the efficacy of the medicament.

Figure 8A:
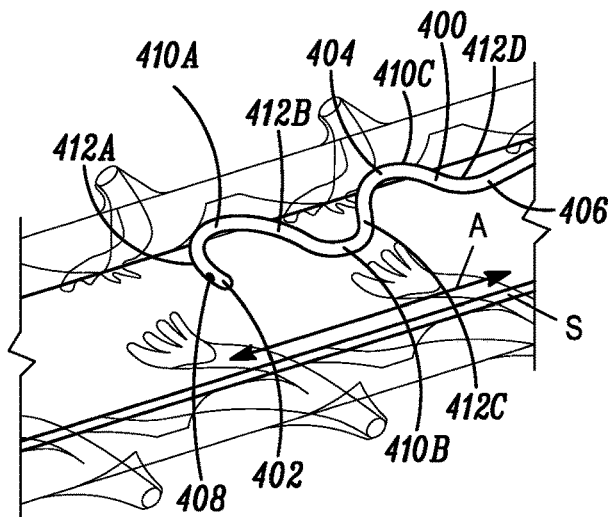
FIG. 8A is a perspective view depicting a catheter in accordance with a second embodiment of the disclosure inserted into a subarachnoid space of a patient.

Referring to FIG. 8A, a catheter 400 configured for increased intrathecal drug dispersion is depicted in accordance with a second embodiment of the disclosure. Catheter 400 can generally include a circular cross-section, and can extend between a proximal end and a distal tip 402. Catheter 400 can generally include a wall 404 defining a lumen 406 extending between the proximal end and a medicament exit 408. Catheter 400 can include multiple features 410A, 410B, and 410C configured to generate vortices within the cerebrospinal fluid for the purpose of improving intrathecal drug dispersion. For example, catheter 400 can be configured to assume a sinusoidal shape, such that multiple portions 412A, 412B, 412C, 412D of the catheter 400 can be positioned at an acute, obtuse, or substantially orthogonal angle relative to the flow of cerebrospinal fluid within the subarachnoid space. Accordingly, the medicament exit 408, which can be positioned proximally from the distal tip 402 along the wall 404 of the catheter 400 can be positioned to expel medicament substantially in-line with the longitudinal axis A of the patient's spinal column S. In one embodiment, the catheter 400 can include multiple medicament exits oriented in different directions or extending along the length of the catheter 400.

Figure 8B:
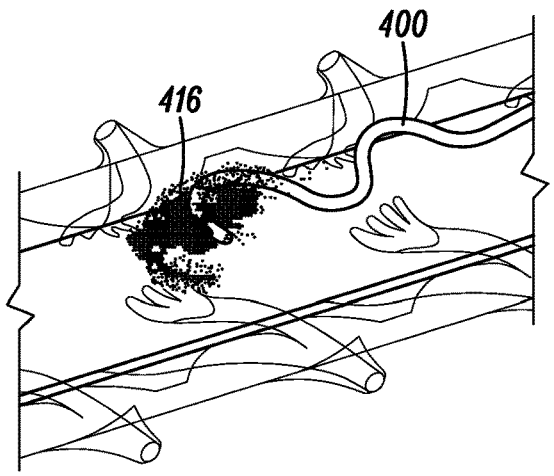
FIG. 8B depicts the dispersion of medicament within the cerebrospinal fluid of a patient after approximately 7.5 seconds of initiating infusion from the catheter of FIG. 8A at a rate of 1 mL per hour.
Figure 8C:
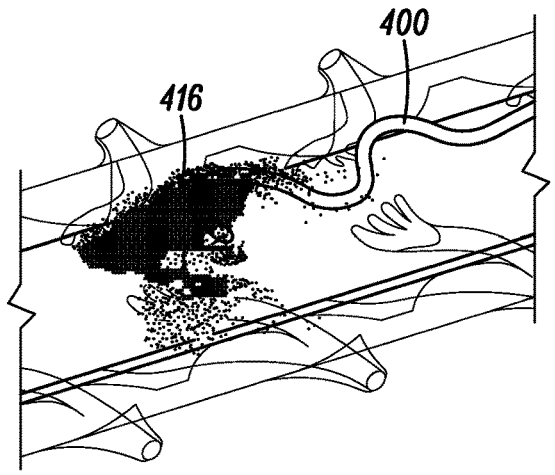
FIG. 8C depicts the dispersion of medicament within the cerebrospinal fluid of a patient after approximately 15 seconds of initiating infusion from the catheter of FIG. 8A at a rate of 1 mL per hour.

FIGS. 8B and 8C depict the catheter 400 as the medicament 416 exits the medicament exit 408 and flows into the subarachnoid space. Specifically, FIG. 8B depicts the dispersion of medicament 416 after approximately 7.5 seconds of initiating infusion, and FIG. 8C depicts the dispersion of medicament 416 after approximately 15 seconds of initiating infusion. As the medicament 416 exits the medicament exit 408 and flows into the subarachnoid space, the medicament 416 begins mixing with the cerebrospinal fluid. Upon infusion, mixing of the medicament 416 with the cerebrospinal fluid is initially promoted by the vortices associated with portion 412A and feature 410A. Mixing up the medicament with the cerebrospinal fluid is subsequently promoted by portions 412B, 412C and 412D and features 410B and 410C, which serve to further promote a mixing effect within the cerebrospinal fluid. Accordingly, intrathecal infusion via catheter 400 enables dispersion of the medicament 416 to occur more rapidly than infusion via conventional methods.

FIGS. 9-12B depict alternative embodiments of catheters 500, 600, 700, 800 including one or more features 502, 602, 702, 802 configured to generate vortices within the cerebrospinal fluid of a patient for the purpose of improving the dispersion of intrathecally administered medicament. In embodiments, the one or more features 502, 602, 702, 802 can be positioned between a distal tip 504, 604, 704, 804 and a medicament exit 506, 606, 706, 806 defined by the catheter wall 508, 608, 708, 808. Other configurations are also contemplated.

Figure 9:
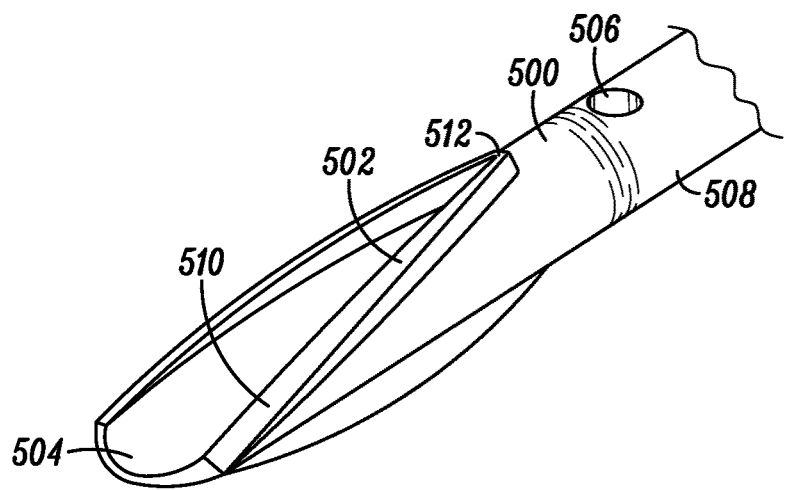
FIG. 9 is a perspective view depicting a catheter in accordance with a third embodiment.
Figure 10:
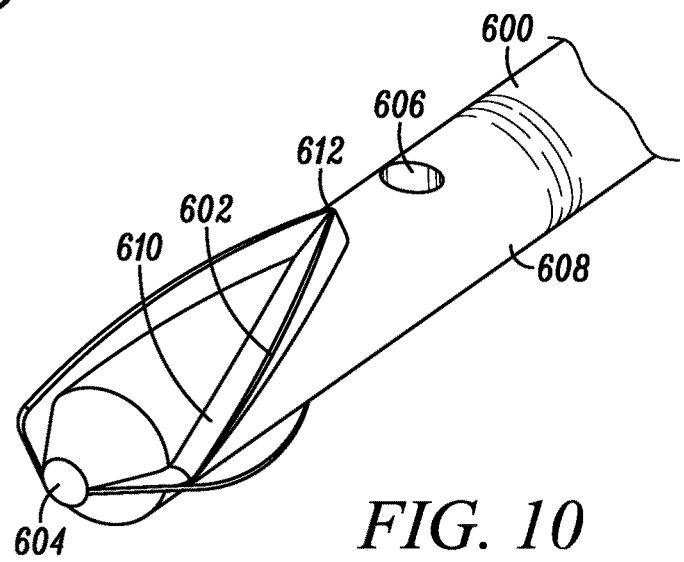
FIG. 10 is a perspective view depicting a catheter in accordance with a fourth embodiment.

For example, in the embodiments depicted in FIGS. 9 and 10, the one or more features 502, 602 can be in the form of a V-shaped ridge 510, 610 originating in proximity to the distal tip 504, 604 and terminating at an apex 512, 612 in proximity to the medicament exit 506, 606. In some embodiments, the catheter 500, 600 can include a pair of V-shaped ridges 510, 610 positioned on opposing lateral sides of the catheter 500, 600. In operation, the V-shaped ridge 510, 610 can interact with medicament expelled from the medicament exit 506, 606, so as to promote separation of the medicament from the slow-moving cerebrospinal fluid immediately surrounding the catheter 500, 600, as well as generate vortices within the cerebrospinal fluid surrounding the catheter 500, 600. In some embodiments, the distal tip 504 can be pointed or otherwise formed as a wedge. In some embodiments, the distal tip 604 can be blunt or otherwise assume a frusto-conical shape.

Figure 11:
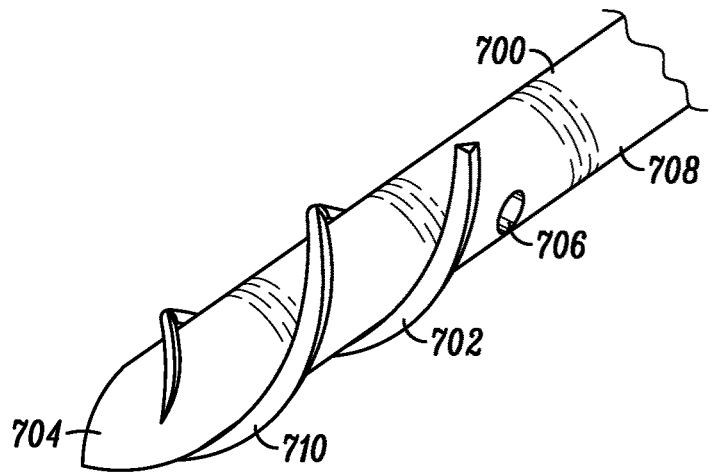
FIG. 11 is a perspective view depicting a catheter in accordance with a fifth embodiment.

In the embodiment depicted in FIG. 11, the one or more features 702 can be in the form of a spiral ridge 710 originating in proximity to the distal tip 704 and terminating in proximity to the medicament exit 706. In operation, the spiral ridge 710 generates vortices within the cerebrospinal fluid surrounding the catheter 700, thereby promoting faster mixing of the medicament expelled from the medicament exit 706 with the cerebrospinal fluid.

Figure 12A:
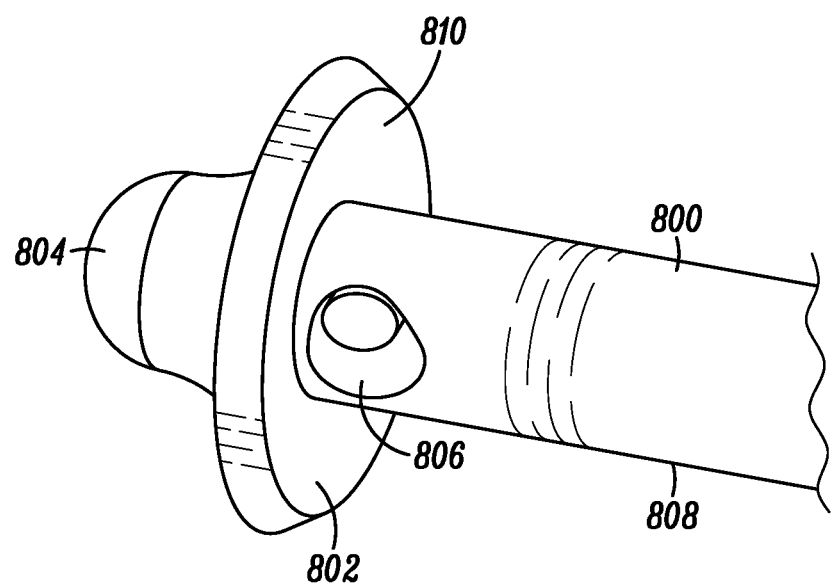
FIG. 12A is a perspective view depicting a catheter in accordance with a sixth embodiment.
Figure 12B:
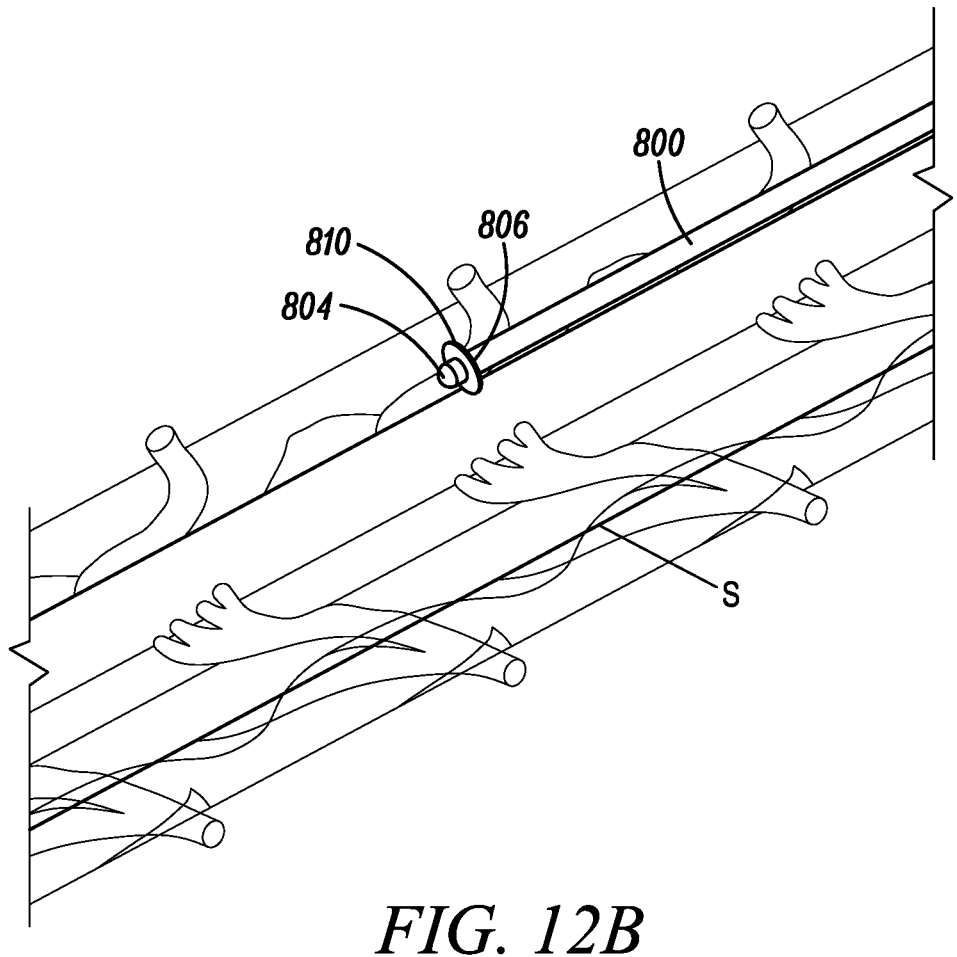
FIG. 12B is a perspective view depicting the catheter of FIG. 12A inserted into a subarachnoid space of a patient.

In the embodiment depicted in FIGS. 12A-B, the one or more features 802 can be in the form of a shelf 810 at least partially surrounding the wall 808 of the catheter 800. In operation, the shelf 810 can present a barrier to inhibit fluid from traversing along a boundary layer, and to generate vortices in the vicinity of the medicament exit 806, thereby improving local mixing of the medicament with the cerebrospinal fluid.

Predictions of the respective volumes of dispersed clouds of medicament for catheters 500, 600, 700, and 800 having one or more features 502, 602, 702, and 802 (such as that depicted in FIGS. 9-12B), with the same model parameters described above, can have an infused medicament volume of approximately 100 mm$^3$. Accordingly, in comparison to a nominal straight catheter 200 (such as that depicted in FIGS. 4A-C), the one or more features 502, 602, 702, and 802 can have the effect of increasing the volume of dispersed medicament approximately 4 times that of prior art designs after 30 seconds of infusion.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. An intrathecal medicament-delivery system configured to disperse a medicament into a cerebrospinal fluid (CSF) in a subarachnoid space of a patient, the system comprising:
    an implantable medical pump; and
    a catheter comprising:
        a distal portion comprising a first outer surface and a medicament exit configured to release the medicament into the CSF, wherein the medicament exit is in fluid communication with the implantable medical pump; and
        a proximal portion comprising a second outer surface, wherein, while the proximal portion and the distal portion are positioned within the subarachnoid space:
            the second outer surface is oriented substantially parallel to a natural flow direction of the CSF; and
            the first outer surface is oriented substantially non-parallel to the natural flow direction, such that interactions between the CSF and the first outer surface generate vortices of CSF to accelerate dispersal of the medicament into the CSF.

2. The system of claim 1, wherein the catheter further comprises a curved portion disposed between the proximal portion and the distal portion, and wherein the curved portion is configured to orient the first outer surface of the distal portion of the catheter at an angle with respect to the second outer surface of the proximal portion of the catheter.

3. The system of claim 2, wherein the curved portion orients the first outer surface of the distal portion substantially orthogonal to the natural flow direction of the CSF.

4. The system of claim 1, wherein the vortices of CSF comprise von Kármán vortex streets within the CSF.

5. The system of claim 1, wherein the first outer surface of the distal portion is configured to induce turbulence within the CSF, wherein the turbulence comprises the vortices of CSF.

6. The system of claim 1, wherein the first outer surface of the distal portion defines the medicament exit at a position at which the catheter releases the medicament substantially parallel to the natural flow direction of the CSF.

7. The system of claim 1, wherein the catheter is configured to convert between a substantially linear insertion configuration and a non-linear infusion configuration.

8. The system of claim 1, wherein the distal portion is sinusoidal shaped.

9. The system of claim 8, wherein the first outer surface of the distal portion defines a plurality of points oriented substantially orthogonal to the natural flow direction of the CSF.

10. The system of claim 1, wherein the distal portion of the catheter further comprises a V-shaped ridge, a spiral ridge, or a radial shelf configured to generate the vortices of CSF.

11. The system of claim 1, wherein each vortex of CSF defines a rotational axis oriented substantially orthogonal to the natural flow direction of the CSF.

12. The system of claim 1, wherein the first outer surface of the distal portion of the catheter defines the medicament exit.

13. The system of claim 1, wherein the medicament exit comprises a single circular aperture.

* * * * *